United States Patent
Zhang et al.

(10) Patent No.: US 10,622,676 B2
(45) Date of Patent: Apr. 14, 2020

(54) FUNCTIONAL ORGANIC SALT FOR LITHIUM-ION BATTERIES

(71) Applicant: UCHICAGO ARGONNE, LLC, Chicago, IL (US)

(72) Inventors: Lu Zhang, Lisle, IL (US); Jingjing Zhang, Willowbrook, IL (US); Ilya A. Shkrob, Chicago, IL (US)

(73) Assignee: UCHICAGO ARGONNE, LLC, Chicago, IL (US)

( * ) Notice: Subject to any disclaimer, the term of this patent is extended or adjusted under 35 U.S.C. 154(b) by 142 days.

(21) Appl. No.: 15/637,188

(22) Filed: Jun. 29, 2017

(65) Prior Publication Data

US 2019/0006712 A1  Jan. 3, 2019

(51) Int. Cl.
| | |
|---|---|
| *H01M 10/0567* | (2010.01) |
| *H01M 10/0525* | (2010.01) |
| *H01M 10/0568* | (2010.01) |
| *C07C 211/36* | (2006.01) |
| *C07C 317/04* | (2006.01) |
| *H01M 10/0569* | (2010.01) |

(52) U.S. Cl.
CPC ....... *H01M 10/0567* (2013.01); *C07C 211/36* (2013.01); *C07C 317/04* (2013.01); *H01M 10/0525* (2013.01); *H01M 10/0568* (2013.01); *C07C 2601/02* (2017.05); *H01M 10/0569* (2013.01); *H01M 2300/0037* (2013.01)

(58) Field of Classification Search
CPC .............................................. H01M 10/0567
See application file for complete search history.

(56) References Cited

U.S. PATENT DOCUMENTS

| | | | |
|---|---|---|---|
| 5,709,968 A | 1/1998 | Shimizu | |
| 7,255,963 B2 * | 8/2007 | Nagayama | H01M 4/131 429/223 |
| 7,297,289 B2 * | 11/2007 | Sato | C07C 217/08 252/62.2 |
| 7,482,090 B2 * | 1/2009 | Tatebayashi | H01M 2/263 429/60 |
| 7,582,386 B2 * | 9/2009 | Takami | H01M 2/1077 429/218.1 |
| 2006/0199080 A1 | 9/2006 | Amine et al. | |
| 2006/0263695 A1 | 11/2006 | Dahn et al. | |
| 2007/0092802 A1 | 4/2007 | Ahn et al. | |
| 2008/0220335 A1 | 9/2008 | Casteel | |

(Continued)

FOREIGN PATENT DOCUMENTS

WO    WO-2012169909 A1 * 12/2012 ........... C07C 211/40

OTHER PUBLICATIONS

Abraham, K.M. et al., n-Butylferrocene for Overcharge Protection of Secondary Lithium Batteries, Journal of the Electrochemical Society, 137 (6), 1856-1857 (1990).

(Continued)

*Primary Examiner* — Ula C Ruddock
*Assistant Examiner* — Thomas H. Parsons
(74) *Attorney, Agent, or Firm* — Olson & Cepuritis, Ltd.; Robert J. Ross

(57) ABSTRACT

An electrolyte for a lithium-ion electrochemical cell comprises a non-aqueous solution of a lithium salt and a redox shuttle salt compound in a non-aqueous solvent, wherein the redox shuttle compound comprises an amino-substituted cyclopropenium salt of Formula (I) as described herein.

20 Claims, 4 Drawing Sheets

(I)

CP-Cl

CP-TSFI

(56) References Cited

U.S. PATENT DOCUMENTS

2013/0189571 A1     7/2013    Abouimrane et al.
2017/0062862 A1     3/2017    Zhang et al.

OTHER PUBLICATIONS

Behl, W. K. et al., Electrochemical Overcharge Protection of Rechargeable Lithium Batteries, I. Kinetics of Iodide/Tri-Iodide/Iodine Redox Reactions on Platinum LiAsF6/Tetrahydrofuran Solutions, Journal of the Electrochemical Society, 135 (1), 16-21 (1988).

Behl, W. K. et al., Electrochemical Overcharge Protection of Rechargeable Lithium Batteries, II. Effect of Lithium Iodide-Iodine Additives on the Behavior of Lithium Electrode in LiAsF6-Tetrahydrofuran Solutions, Journal of the Electrochemical Society, 135 (1), 21-25 (1988).

Buhrmester C. et al., Studies of Aromatic Redox Shuttle Additives for LiFePO4-Based Li-Ion Cells, Journal of the Electrochemical Society, 152 (12) A2390-A2399 (2005).

Chen, Z. et al., Redox Shuttles for Safer Lithium-Ion Batteries, Electrochimica Acta, 54 (24), 5605-5613 (2009).

Chen, Z. et al., Lithium Borate Cluster Salts as Redox Shuttles for Overcharge Protection of Lithium-Ion Cells, Electrochemical and Solid State Letters, 13 (4), A39-A42 (2010).

Curnow, O.J. et al., Triaminocyclopropenium Salts As Ionic Liquids, Chemical Communication 47, 10248-10250 (2011).

Jiang, Y. et al., The Evolution of Cyclopropenium Ions Into Functional Polyelectrolytes, Nature Communications 6:5950, doi: 10.1038/ncomms6950, 1-7 (2015).

Moshurchak, L.M. et al., High-Potential Redox Shuttle for Use in Lithium-Ion Batteries, Journal of the Electrochemical Society, 156 (4) A309-A312 (2009).

Sevov, C. S. et al., Cyclopropenium Salts as Cyclable, High-Potential Catholytes in Nonaqueous Media, Advanced Energy Materials 1602027, 1-5 (2016).

Wen, J. et al., A Review on Lithium-Ion Batteries Safety Issues: Existing Problems and Possible Solutions, Materials Express 2, (3), pp. 197-212 (2012).

Zhang, L. et al., Redox Shuttle Additives for Lithium-Ion Battery, Lithium Ion Batteries—New Developments 7, 173-189 (2012).

Zhang, L. et al., Molecular Engineering Towards Safer Lithium-Ion Batteries: A Highly Stable and Compatible Redox Shuttle for Overcharge Protection, Energy & Environmental Science 5, 8204-8207 (2012).

Zhang, L. et al., Redox Shuttles for Overcharge Protection of Lithium-Ion Batteries, ECS Transactions 45 (29), 57-66 (2013).

\* cited by examiner

FUNCTIONAL ORGANIC SALT FOR LITHIUM-ION BATTERIES

STATEMENT OF GOVERNMENT INTEREST

The United States Government has rights in this invention pursuant to Contract No. DE-AC02-06CH11357 between the United States Government and UChicago Argonne, LLC representing Argonne National Laboratory.

FIELD OF THE INVENTION

This invention relates to electrolyte additive materials for use in electrochemical cells and batteries. More particularly, this invention relates to redox shuttle electrolyte additive materials for lithium ion batteries.

BACKGROUND

Lithium-ion batteries (LIBs) have been considered as one of the most representative classes of modern secondary batteries since their debut in 1990 due to superior features such as high energy density, high discharge potential, low self-discharge, and no memory effects in comparison to traditional rechargeable cells. The prevalence of lithium-ion batteries in numerous applications from wearable electronics to electric vehicles raises increasing attention to safety issues. One of the major concerns with lithium ion batteries is overcharge, which can result in highly dangerous potential hazards like battery component damage, overheat, burn, and even explosion. Overcharge of lithium-ion batteries is a continuous electricity input to cells when full capacity has been reached. Instead of being stored in the electrode, redundant electric energy resulting from overcharge tends to accumulate on the surface of the electrode and elevate the potential dramatically, leading to exothermic reactions of electrolytes and other battery components that are electrochemically inert in normal the potential range of the charging process. Currently, most practical overcharge protection methods can be categorized into two major types: (1) electronic overvoltage cut-off devices, and (2) redox shuttle additives for chemical overcharge protection. It is noteworthy that the second type has elicited particular attention from researchers due to a number of comparative advantages including lower cost, minimized additional weight and volume, and inherent overcharge suppression.

Generally, the redox shuttle molecule can be reversibly oxidized and reduced at a defined potential slightly higher than the end-of-charge potential of the cathode. This mechanism can protect the cell from overcharge by locking the potential of the cathode at the oxidation potential of the shuttle molecules. On the overcharged cathode surface, the redox shuttle molecule (S) is oxidized to its (radical) cation form (S•+), which, via diffusion through the electrolyte, is reduced back to its original or reduced state on the surface of the anode. The reduced form can then diffuse back to the cathode and oxidize again. The "oxidation-diffusion-reduction-diffusion" cycle can be repeated continuously due to the reversible nature of the redox shuttle to shunt the overcharge current. The redox shuttling mechanism at overcharge can be regarded as a controlled internal short, and the net result of the shuttling is to convert the overcharge electricity power into heat, which avoids the reactions that occur between the electrodes and electrolyte at high voltage. Redox shuttles can also be used for automatic capacity balancing during battery manufacturing and repair. Modern LIB designs are challenging the limits of current redox shuttle materials.

Ideal redox shuttle additives are materials that can be readily dissolved in electrolyte and have appropriate oxidation potential (approximately 0.3-0.5 V higher than that of the cathode) while maintaining high electrochemical stability. Once the potential of the cathode exceeds the potential of redox shuttle additives, initially unreactive shuttle molecules will be electrochemically activated, and start to take over the oxidative electrons. As a result, the potential of the cell remains unchanged in this process. Redox shuttle additives in the oxidative state then diffuse to the anode and get reduced to the initial state, which will transport back to the cathode. Therefore, this sustainable circle of redox shuttle additives prevents potential hazards of overcharge by fixing the cathode potential at their oxidation potential. Although a large variety of materials have been attempted to serve this purpose, it still remains a great challenge to develop shuttle additives featuring high solubility, suitable oxidation potential, and high electrochemical stability in one system. To this day, one of the most promising additives is 2,5-di-tert-butyl-1,4-bis(2-methoxyethoxy)benzene (DBBB), which has an oxidation potential at 3.98 V vs. Li/Li$^-$ and undergoes overcharge abuse for over 3000 hours before a significant drop in performance is observed. One possible reason for the eventual performance drop is believed to be the consumption of redox shuttle additives through reactions between the two unsubstituted positions on the radical cation after oxidation.

There is an ongoing need for new redox shuttle chemistries to ameliorate the overcharge phenomenon in lithium-ion batteries. The redox shuttle additives described herein address this need.

SUMMARY

An electrolyte for a lithium-ion electrochemical cell is described herein. The electrolyte comprises a non-aqueous solution of a lithium salt and a redox shuttle salt. The redox shuttle salt comprises a compound of Formula (I):

wherein $X^\ominus$ is an anion selected from a halide, bis(trifluoromethanesulfonyl)imidate, tetrafluoroborate, hexafluorophosphate, and an anion of Formula (II):

wherein Z is selected from alkylsulfonyl, alkylcarbonyl, fluorinated-alkylsulfonyl, and fluorinated-alkylcarbonyl; R and R' are independently selected from alkyl, aryl, alkylaryl, and poly(alkylene glycol) groups. The alkyl, aryl, arylalkyl and alkylaryl groups optionally can be substituted by one of more substituent selected from halogen, hydroxyl, alkoxy, alkylsulfonyl, arylsulfonyl, and the like.

The following non-limiting examples of embodiments of the electrolytes and materials described herein are provided to illustrate certain features and expects of the present invention.

Embodiment 1 is an electrolyte for a lithium-ion electrochemical cell comprising a non-aqueous solution of a lithium salt and a redox shuttle salt; wherein the redox shuttle salt comprises a compound of Formula (I) as described herein.

Embodiment 2 is the electrolyte of Embodiment 1, wherein R and R' independently are $C_1$ to $C_8$ alkyl.

Embodiment 3 is the electrolyte of Embodiment 1 or Embodiment 2, wherein R and R' are ethyl.

Embodiment 4 is the electrolyte of any one of Embodiments 1 through 3, wherein $X^\ominus$ is a halide.

Embodiment 5 is the electrolyte of any one of Embodiments 1 through 4, wherein $X^\ominus$ is chloride.

Embodiment 6 is the electrolyte of any one of Embodiments 1 through 5, wherein $X^\ominus$ is a sulfonimidate anion.

Embodiment 7 is the electrolyte of any one of Embodiments 1 through 6, wherein $X^\ominus$ is an anion of Formula (II):

(II)

wherein Z is selected from alkylsulfonyl, alkylcarbonyl, fluorinated-alkylsulfonyl, and fluorinated-alkylcarbonyl.

Embodiment 8 is the electrolyte of any one of Embodiments 1 through 7, wherein $X^\ominus$ is bis(trifluoromethanesulfonyl)imidate anion.

Embodiment 9 is the electrolyte of any one of Embodiments 1 through 8, wherein the compound of Formula (I) comprises tris(diethylamino)cyclopropenium chloride (CP-Cl), which has the formula:

CP-Cl

Embodiment 10 is the electrolyte of any one of Embodiments 1 through 9, wherein the compound of Formula (I) comprises tris(diethylamino)cyclopropenium bis(trifluoromethanesulfonyl)imidate (CP-TSFI), which has the formula:

CP-TSFI

Embodiment 11 is the electrolyte of any one of Embodiments 1 through 10, wherein the lithium salt comprises one or more of lithium bis(trifluoromethanesulfonyl)imidate (LiTFSI), lithium 2-trifluoromethyl-4,5-dicyanoimidazolate (LiTDI), lithium 4,5-dicyano-1,2,3-triazolate (LiTDI), lithium trifluoromethanesulfonate (LiTf), lithium perchlorate ($LiClO_4$), lithium bis(oxalato)borate (LiBOB), lithium difluoro(oxalato)borate (LiDFOB), lithium tetrafluoroborate ($LiBF_4$), lithium hexafluorophosphate ($LiPF_6$), lithium thiocyanate (LiSCN), lithium bis(fluorosulfonyl)imidate (LIFSI), lithium bis(pentafluoroethylsulfonyl)imidate (LBETI), lithium tetracyanoborate ($LiB(CN)_4$), and lithium nitrate.

Embodiment 12 is the electrolyte of any one of Embodiments 1 through 11, wherein the lithium salt is present in the electrolyte at a concentration in the range of about 0.1 M to about 3 M.

Embodiment 13 is the electrolyte of any one of Embodiments 1 through 12, wherein the compound of Formula (I) is present in the electrolyte at a concentration in the range of about 0.005 M to about 0.5 M.

Embodiment 14 is the electrolyte of any one of Embodiments 1 through 13, wherein the non-aqueous solvent comprises one or more of an ether, a carbonate ester, a nitrile, a sulfoxide, a sulfone, a fluoro-substituted linear dialkyl carbonate, a fluoro-substituted cyclic alkylene carbonate, a fluoro-substituted sulfolane, and a fluoro-substituted sulfone.

Embodiment 15 is the electrolyte of any one of Embodiments 1 through 14, wherein the non-aqueous solvent comprises one or more carbonate esters selected from ethylene carbonate, propylene carbonate, dimethyl carbonate, diethyl carbonate, and ethylmethyl carbonate.

Embodiment 16 is the electrolyte of any one of Embodiments 1 through 15, wherein the non-aqueous solvent comprises ethylene carbonate (EC) and ethyl methyl carbonate (EMC) in an EC:EMC ratio of about 3:7 (v:v).

Embodiment 17 is the electrolyte of any one of Embodiments 1 through 15, wherein the lithium salt comprises about 1 to 1.5 M $LiPF_6$ and the compound of Formula (I) comprises about 0.3 to 0.5 M CP-Cl.

Embodiment 18 is the electrolyte of any one of Embodiments 1 through 15, wherein the lithium salt comprises about 1 to 1.5 M $LiPF_6$ and the compound of Formula (I) comprises about 0.3 to 0.5 M CP-TFSI.

Embodiment 19 is an electrochemical cell comprising an anode, a cathode, a lithium ion-porous membrane between the anode and the cathode, and the electrolyte of any one of Embodiments 1 through 18 contacting the anode, the cathode, and the membrane.

Embodiment 20 is a battery comprising a plurality of electrochemical cells of Embodiment 19 electrically connected together in series, in parallel, or in both series and parallel.

The redox shuttle salts described herein provide overcharge protection to lithium-ion batteries without causing any modifications on the cell architecture. Redox shuttles represent electrochemically reversible materials that have suitable redox potential (approximately 0.3-0.5 V higher than the end of the charge potential of the cathode) and can be readily dissolved in the electrolyte while retaining high electrochemical stability. However, most reported shuttle molecules often introduce higher viscosity and lower conductivity to the lithium-ion batteries, which significantly limits their further applicability. The class of tris(dialkylamino)cyclopropenium salt-based ionic liquids described herein demonstrate excellent and surprising chemical and electrochemical stability, high electrochemical reversibility with appropriate oxidation potential, and unprecedentedly high solubility. These materials, in particular, ameliorate drawbacks of conventional organic small molecule-based shuttles.

BRIEF DESCRIPTION OF THE DRAWINGS

The invention consists of certain novel features and a combination of parts hereinafter fully described, illustrated in the accompanying drawings, it being understood that various changes in the details may be made without departing from the spirit, or sacrificing any of the advantages of the present invention.

DETAILED DESCRIPTION OF SELECTED EMBODIMENTS

Described herein are non-aqueous electrolytes for a lithium-ion batteries comprising a lithium salt and a redox shuttle salt additive in a non-aqueous solvent. The redox shuttle salt additives are tris(amino)-substituted cyclopropenium salts of Formula (I).

(I)

wherein $X^\ominus$ is an anion. In some embodiments $X^\ominus$ is an anion selected from a halide (e.g., $F^-$, $Cl^-$, $Br^-$), bis(trifluoromethanesulfonyl)imidate, tetrafluoroborate, hexafluorophosphate and an anion of Formula (II):

(II)

wherein Z is selected from alkylsulfonyl, alkylcarbonyl, fluorinated-alkylsulfonyl, and fluorinated-alkylcarbonyl; (e.g., bis(methylsulfonyl)imidate, bis(trifluoromethanesulfonyl)imidate, bis(trifluoroacetyl)imidate, and the like). In some preferred embodiments $X^\ominus$ is chloride or bis(trifluoromethanesulfonyl)imidate.

R and R' are independently selected from alkyl (e.g., $C_1$ to $C_8$ alkyl, such as methyl, ethyl, propyl, isopropyl, butyl, pentyl, and the like), aryl (e.g., phenyl), arylalkyl (e.g., benzyl, 2-phenylethyl, and the like), alkylaryl (e.g., $C_1$ to $C_8$ alkyl-substituted phenyl, such as 4-ethylphenyl, 2,4,6-trimethylphenyl, and the like), and a poly(alkylene glycol) group. As used herein the term poly(alkylene glycol) refers to an oligomer or polymer of alkylene glycol monomer units (e.g., an ethylene glycol polymer or oligomer, a propylene glycol polymer or oligomer, an ethylene glycol-propylene glycol copolymer, and the like). For example, a poly(alkylene glycol) group for use as a substituent R or R' can have the formula: —C(R")$_2$—C(R")$_2$—(O—C(R")$_2$—C(R")$_2$)$_n$—OC(R")$_2$—C(R")$_2$—OR'" where R'" can be H, methyl, or ethyl, and n is 3 to 100. In some preferred embodiments, R and R' are independently $C_1$ to $C_4$ alkyl (e.g., methyl, ethyl, propyl, isopropyl and t-butyl).

The redox shuttle salt additive can be present in the electrolyte at any concentration, but preferably is present at a concentration in the range of about 0.005 M to about 0.5 M. In some embodiments, the additive is present in the electrolyte at a concentration in the range of about 0.01 M to about 0.4 M, or about 0.03 M to about 0.3 M.

The electrolyte can include any lithium salt that is suitable for use as a lithium ion source in electrolytes for lithium-ion batteries, which salts are well known in the secondary battery art. Non-limiting examples of lithium salts useful in the electrolyte compositions described herein include, e.g., lithium bis(trifluoromethanesulfonyl)imidate (LiTFSI), lithium 2-trifluoromethyl-4,5-dicyanoimidazolate (LiTDI), lithium 4,5-dicyano-1,2,3-triazolate (LiTDI), lithium trifluoromethanesulfonate (LiTf), lithium perchlorate (LiClO$_4$), lithium bis(oxalato)borate (LiBOB), lithium difluoro(oxalato)borate (LiDFOB), lithium tetrafluoroborate (LiBF$_4$), lithium hexafluorophosphate (LiPF$_6$), lithium thiocyanate (LiSCN), lithium bis(fluorosulfonyl)imidate (LIFSI), lithium bis(pentafluoroethylsulfonyl)imidate (LBETI), lithium tetracyanoborate (LiB(CN)$_4$), lithium nitrate, combinations of two or more thereof, and the like. In some preferred embodiment, the lithium salt comprises lithium nitrate in combination with at least one other salt, e.g., LiTFSI. Preferably, the lithium salt is selected from one or more of LiF$_2$BC$_2$O$_4$, LiPF$_6$, LiBF$_4$, LiB(C$_2$O$_4$)$_2$, LiClO$_4$, lithium bis(fluorosulfonyl)imidate (LiFSI), lithium bis(trifluoromethanesulfonyl)imidate (LiTFSi), and LiAsF$_6$. The lithium salt can be present in the electrolyte at any concentration suitable for lithium-ion battery applications, which concentrations are well known in the secondary battery art. In some embodiments, the lithium salt is present in the electrolyte at a concentration in the range of about 0.1 M to about 3 M, e.g., about 0.5 M to 2 M, or 1 M to 1.5M.

The electrolyte comprises a non-aqueous solvent, wherein the solvent comprises one or more solvent compound selected from an ether, a carbonate ester, a nitrile, a sulfoxide, a sulfone, a fluoro-substituted linear dialkyl carbonate, a fluoro-substituted cyclic alkylene carbonate, a fluoro-substituted sulfolane, and a fluoro-substituted sulfone. For example, the solvent can comprise an ether (e.g., glyme or diglyme), a linear dialkyl carbonate (e.g., dimethyl carbonate (DMC), diethyl carbonate (DEC), ethyl methyl carbonate (EMC) and the like), a cyclic alkylene carbonate (ethylene carbonate (EC), propylene carbonate (PC) and the like), a sulfolane (e.g., sulfolane or an alkyl-substituted sulfolane), a sulfone (e.g., a dialkyl sulfone such as a methyl ethyl sulfone), a fluoro-substituted linear dialkyl carbonate, a fluoro-substituted cyclic alkylene carbonate, a fluoro-substituted sulfolane, and a fluoro-substituted sulfone. The solvent can comprise a single solvent compound or a mixture of two or more solvent compounds. in some embodiments, the solvent comprises a mixture of a cyclic alkylene carbonate and a linear dialkyl carbonate, for example, a mixture of ethylene carbonate and ethyl methyl carbonate (EC/EMC), e.g., in a weight to weight ratio of about 3:7 EC:EMC.

The electrolytes can be incorporated in a lithium ion electrochemical cell comprising a positive electrode (cathode), a negative electrode (anode), and a porous separator between the cathode and anode, with the electrolyte in contact with both the anode and cathode, as is well known in the battery art. A battery can be formed by electrically connecting two or more such electrochemical cells in series, parallel or a combination of series and parallel. The electrolyte can be utilized with any anode or cathode compositions useful in lithium-ion batteries. Electrochemical cell and battery designs and configurations, anode and cathode materials, as well as electrolyte salts, solvents and other battery or electrode components (e.g., separator membranes, current collectors), which can be used in the electrolytes, cells and batteries described herein, are well known in the lithium battery art, e.g., as described in "Lithium Batteries Science and Technology" Gholam-Abbas Nazri and Gianfranco Pistoia, Eds., Springer Science+Business Media, LLC; New York, N.Y. (2009), which is incorporated herein by reference in its entirety.

The following non-limiting examples illustrate various features of the electrolytes and materials described herein, as well as methods of synthesizing such compounds.

EXAMPLE 1

Synthesis of Redox Shuttle Additives

A. Synthesis of tris(diethylamino)cyclopropenium chloride (CP-Cl).

57%

To 10 mL of dry dichloromethane was added pentachlorocyclopropane (3.3 g, 15.4 mmol) at 0° C. Diethylamine (7.9 g, 108 mmol) was slowly added to the solution over 1 hour. The reaction mixture was vigorously stirred for 4 hours at 0° C. and then at room temperature for 18 hours before heating to 65° C. The reaction mixture was cooled to room temperature and precipitated with 30 mL of acetone and the diethylammonium chloride salt byproduct was removed by filtration as a white solid. This purification process was repeated for three times. The supernatant was concentrated in vacuo to yield tris(diethylamino)cyclopropenium chloride as an orange oil (2.5 g, 56.5%). $^1$H NMR (CDCl$_3$, 300 MHz): δ (ppm) 3.42-3.49 (q, J=7.2 Hz, 12H), 1.28-1.33 (t, J=7.3 Hz, 18H); $^{13}$C NMR (CDCl$_3$, 75 MHz): δ (ppm) 116.1, 47.2, 14.4.

B. Synthesis of tris(diethylamino)cyclopropenium bis(trifluoromethanesulfonyl)imidate (CP-TFSI).

54%

To the solution of CP-Cl (1.2 g, 4.17 mmol) in 40 mL of deionized water was added bis(trifluoromethanesulfonyl) imidate lithium salt (3.6 g, 12.5 mmol) at room temperature and the reaction mixture was vigorously stirred overnight. Then the reaction mixture then was extracted with chloroform and washed with water. The organic layer was dried over Na$_2$SO$_4$ and concentrated in vacuo to yield tris(diethylamino)cyclopropenium bis(trifluoro-methanesulfonyl) imidate as an orange-brownish oil (1.2 g, 53.9%). $^1$H NMR (CDCl$_3$, 300 MHz): δ (ppm) 3.36-3.43 (q, J=7.2 Hz, 12H), 1.26-1.64 (t, J=7.3 Hz, 18H); $^{13}$C NMR (CDCl$_3$, 75 MHz): δ (ppm) 116.3, 46.9, 14.1; $^{19}$F NMR (CDCl$_3$, 282 MHz): δ (ppm) 78.8.

EXAMPLE 2

Electrochemical Evaluation of CP-Cl and CP-TFSI in Lithium Ion Cells

All electrodes utilized herein are from the Argonne National Laboratory (ANL) Cell Analysis, Modeling and Prototyping (CAMP) facility.

Coin Cells:

The positive electrode material was composed of about 80 wt % LiFePO$_4$ (LFP), about 8 wt % polyvinylidene fluoride (PVDF) binder, and about 12 wt % carbon black coated on an aluminum current collector. The loading density of the positive electrode active material was about 12.1 mg/cm$^2$. The negative electrode was composed of 87 wt % lithium titanate (Li$_4$Ti$_5$O$_{12}$) (LTO), 5 wt % carbon black, and about 8 wt % PVDF binder coated on a copper current collector. The loading density of the negative electrode active material was about 8 mg/cm$^2$. The separator used in the coin cell assembly was a polypropylene/polyethylene/polypropylene separator (PP/PE/PP; CELGARD 2325). The base electrolyte used was composed of 1.2 M LiPF$_6$ in a mixture of ethylene carbonate (EC) and ethyl methyl carbonate (EMC) in an EC/EMC volume:volume (v:v) ratio of about 3/7), referred to as Electrolyte A herein, and containing the redox shuttle additive at specified concentrations. All electrodes used were dried at 100° C. prior to use and all coin cells were assembled in an argon-atmosphere under constant-temperature (30° C.).

Electrochemical Data:

All coin cell-derived electrochemical data were collected on MACCOR cyclers. Cyclic voltammetry (CV) was performed in Electrolyte A containing the shuttle salt at specified concentrations using a three electrode apparatus with a Pt electrode, a Li counter electrode and a Li reference electrode ("Pt|Li|Li") at various scan rates.

Figure 1:
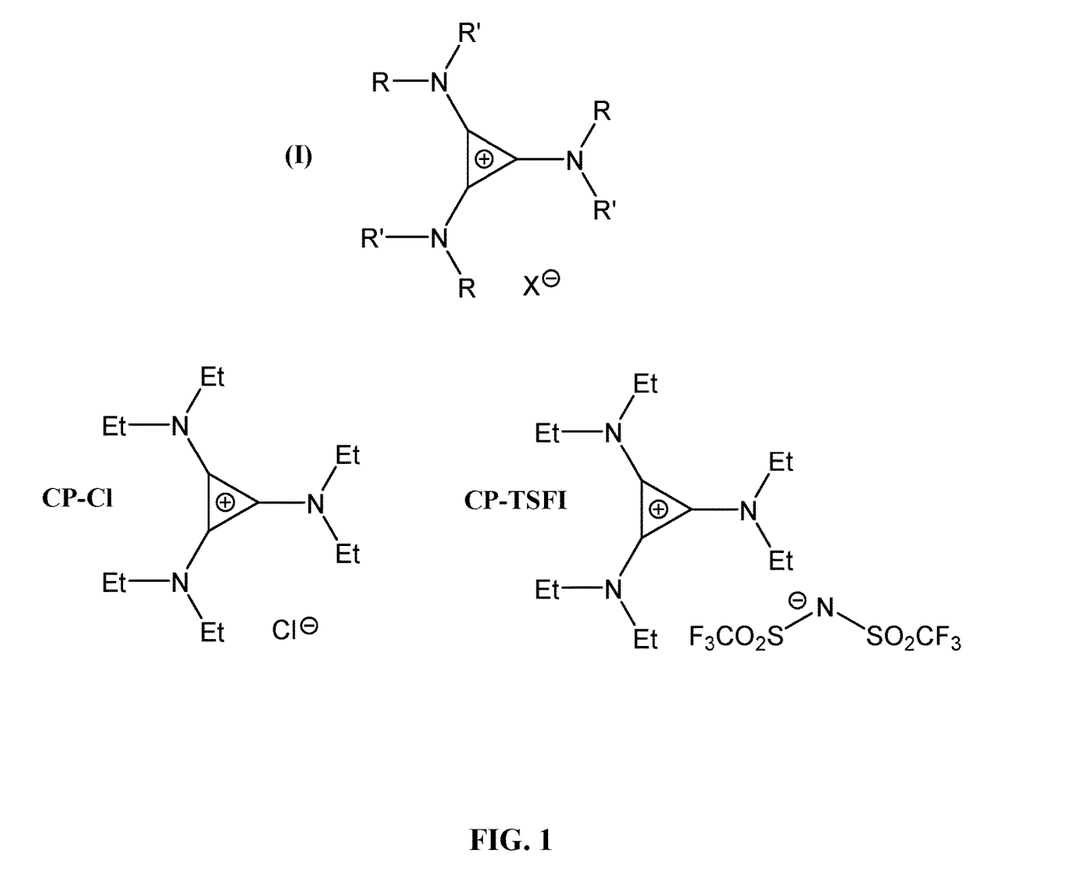
FIG. 1 illustrates compounds of tris(diethylamino)cyclopropenium-type additives of Formula (I) including tris(diethylamino)cyclopropenium chloride (CP-Cl) and tris(diethylamino)cyclopropenium bis(trifluoromethanesulfonyl)imidate (CP-TFSI).
Figure 2:
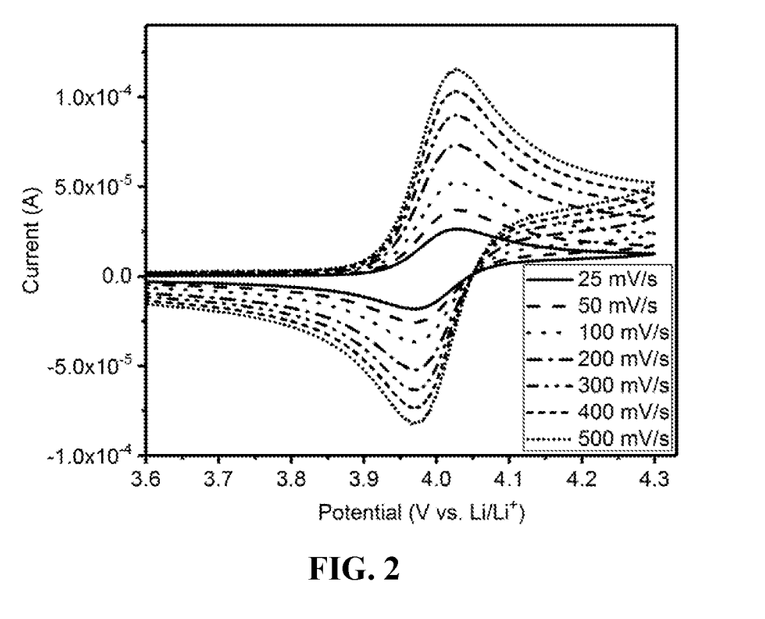
FIG. 2 shows cyclic voltammograms of electrochemical cells utilizing an electrolyte containing CP-Cl (10 mM) at various scan rates.

FIG. 2 shows cyclic voltammograms of CP-Cl (10 mM) in Electrolyte A using the three electrode apparatus (Pt|Li|Li) at various scan rates. One pair of electrochemically reversible peaks was observed between 3.9 and 4.1 V vs Li/Li$^+$, which is well below the stability threshold voltage (about 4.8 V vs. Li/Li$^+$) of common electrolyte components such as ethylene carbonate, propylene carbonate, dimethyl carbonate, and LiPF$_6$. The exceptional electrochemical reversibility of CP-Cl makes this compound useful as a redox shuttle additive for overcharge protection of lithium-ion batteries.

Figure 3:
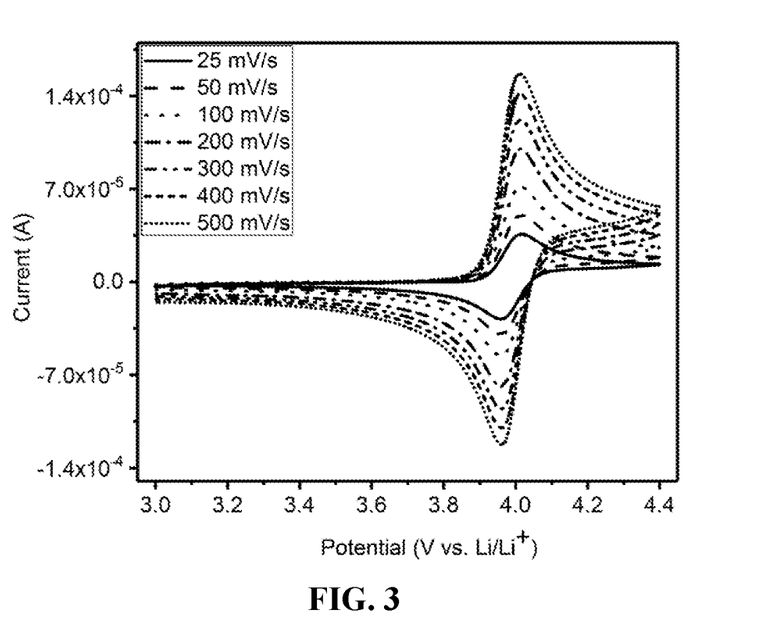
FIG. 3 shows cyclic voltammograms of electrochemical cells utilizing an electrolyte containing CP-TFSI (10 mM) at various scan rates.

FIG. 3 provides cyclic voltammograms of CP-TFSI (10 mM) in Electrolyte A using the three electrode apparatus (Pt|Li|Li) at various scan rates. One pair of electrochemically reversible peaks was observed between 3.9 and 4.1 V vs Li/Li$^+$, which is well below the stability threshold voltage (about 4.8 V vs. Li/Li$^+$) of common electrolyte components such as ethylene carbonate, propylene carbonate, dimethyl carbonate, and LiPF$_6$. The exceptional electrochemical reversibility of CP-TFSI makes this compound useful as a redox shuttle additive for overcharge protection of lithium-ion batteries.

Figure 4:
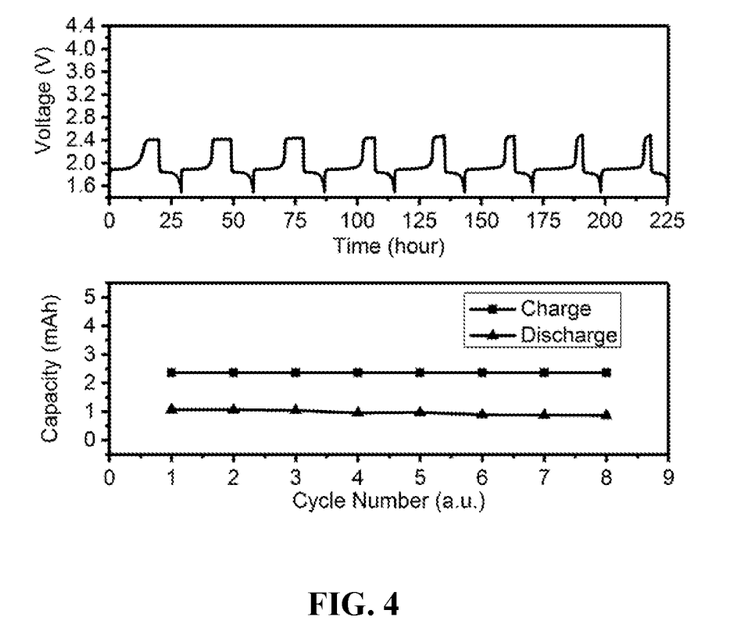
FIG. 4 shows a voltage profile plot of overcharge data (top) and a capacity versus cycling number plot (bottom) from coin cells using an electrolyte containing CP-Cl (0.4 M); charging rate of C/10 and overcharge rate of 100%. The plot shows data for the first 225 hours of cycling.

FIG. 4 shows voltage profiles of overcharge tests of coin cells using an LTO anode and an LFP cathode, and comprising 0.4 M CP-Cl in Electrolyte A, during the course of 225 hours. The charging rate was C/10 and the overcharge rate was 100%. The tris(diethylamino)cyclopropenium chloride additive demonstrated excellent overcharge protection performance in Electrolyte A.

Figure 5:
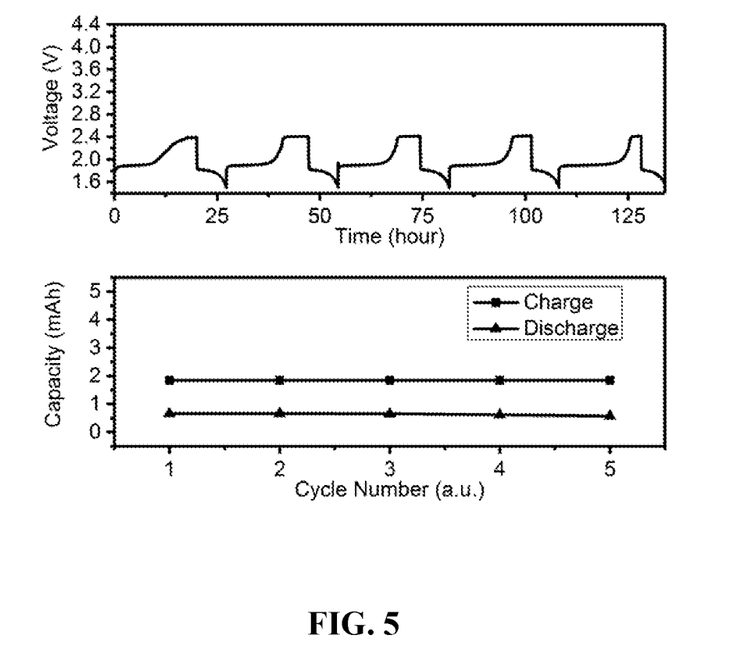
FIG. 5 shows a voltage profile plot of overcharge data (top) and a capacity versus cycling number plot (bottom) from coin cells using an electrolyte containing CP-TFSI (0.4 M); charging rate of C/10 and overcharge rate of 100%. The plot shows data for approximately the first 130 hours of cycling.

FIG. 5. shows voltage profiles of overcharge tests of coin cells using an LTO anode and an LFP cathode, and comprising 0.4 M CP-TFSI in Electrolyte A, during the course of approximately 130 hours. The charging rate was C/10 and the overcharge rate was 100%. The tris(diethylamino)cyclopropenium bis(trifluoromethanesulfonyl) imidate additive demonstrated excellent overcharge protection performance in Electrolyte A.

EXAMPLE 3

Electrochemical Cells

Figure 6:
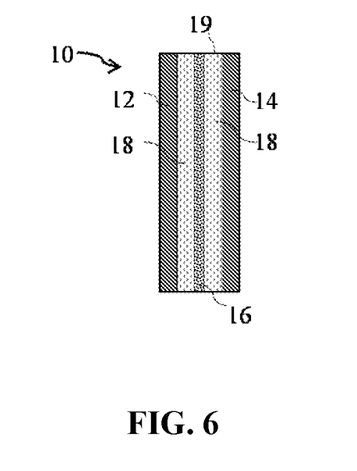
FIG. 6 schematically illustrates a lithium-ion electrochemical cell.
Figure 7:
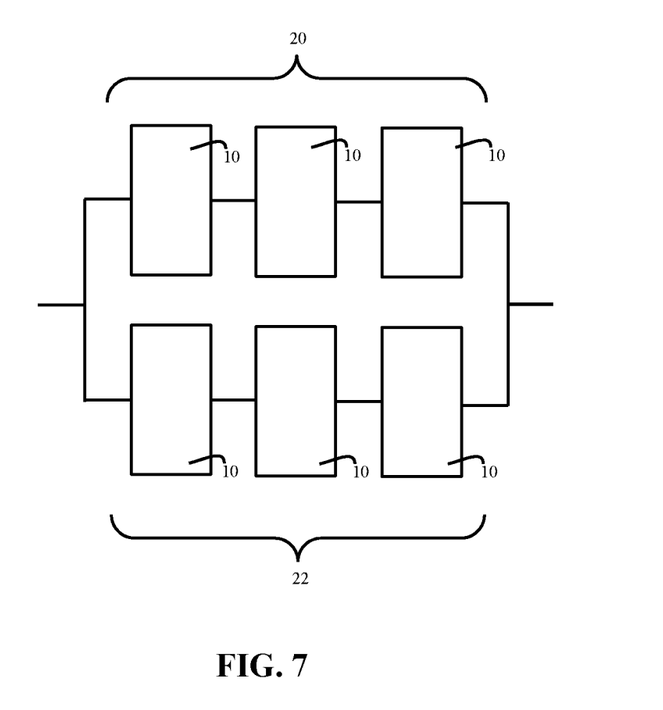
FIG. 7 schematically illustrates a lithium-ion battery.

FIG. 6 schematically illustrates a cross-sectional view of lithium-ion electrochemical cell 10 comprising cathode 12, and anode 14, with porous separator membrane 16 therebetween. Electrolyte 18, comprising a solution of a lithium salt in a non-aqueous solvent containing a redox shuttle additive, contacts electrodes 12 and 14 and separator 16. The electrodes, separator and electrolyte are sealed within housing 19. FIG. 7 schematically illustrates a lithium-ion battery comprising a first array 20 consisting of three series-connected electrochemical cells 10, and a second array 22 consisting of three series-connected electrochemical cells 10, in which first array 20 is electrically connected to second array 22 in parallel.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Embodiments of the invention in which an exclusive property or privilege is claimed are defined as follows:

1. An electrolyte for a lithium-ion electrochemical cell comprising a non-aqueous solution of a lithium salt and a redox shuttle salt in an organic solvent; wherein the redox shuttle salt comprises a compound of Formula (I):

wherein $X^\ominus$ is an anion selected from the group consisting of a halide, and bis(trifluoromethanesulfonyl)imidate, tetrafluoroborate, hexafluorophosphate, and an anion of Formula (II):

Z is selected from the group consisting of alkylsulfonyl, alkylcarbonyl, fluorinated-alkylsulfonyl, and fluorinated-alkylcarbonyl;

R and R' are independently selected from the group consisting of $C_1$ to $C_8$ alkyl, aryl, alkylaryl, and poly(alkylene glycol) groups; and the alkyl, aryl, arylalkyl and alkylaryl groups optionally are substituted by one of more substituent selected from halogen, hydroxyl, alkoxy, alkylsulfonyl, and arylsulfonyl; and wherein the compound of Formula (I) is present in the organic solvent at a concentration in the range of about 0.005 M to about 0.5 M.

2. The electrolyte of claim 1, wherein R and R' are ethyl.

3. The electrolyte of claim 1, wherein $X^\ominus$ is a halide.

4. The electrolyte of claim 1, wherein $X^\ominus$ is chloride.

5. The electrolyte of claim 1, wherein $X^\ominus$ is a sulfonimidate anion.

6. The electrolyte of claim 1, wherein $X^\ominus$ is an anion of Formula (II):

wherein Z is selected from the group consisting of alkylsulfonyl, alkylcarbonyl, fluorinated-alkyl sulfonyl, and fluorinated-alkylcarbonyl.

7. The electrolyte of claim 1, wherein $X^\ominus$ is bis(trifluoromethanesulfonyl)imidate anion.

8. The electrolyte of claim 1, wherein the lithium salt comprises one or more salt selected from the group consisting of lithium bis(trifluoromethanesulfonyl)imidate (LiTFSI), lithium 2-trifluoromethyl-4,5-dicyanoimidazolate (LiTDI), lithium 4,5-dicyano-1,2,3-triazolate (LiTDI), lithium trifluoromethanesulfonate (LiTf), lithium perchlorate (LiClO$_4$), lithium bis(oxalato)borate (LiBOB), lithium difluoro(oxalato)borate (LiDFOB), lithium tetrafluoroborate (LiBF$_4$), lithium hexafluorophosphate (LiPF$_6$), lithium thiocyanate (LiSCN), lithium bis(fluorosulfonyl)imidate (LIFSI), lithium bis(pentafluoroethylsulfonyl)imidate (LBETI), lithium tetracyanoborate (LiB(CN)$_4$), and lithium nitrate.

9. The electrolyte of claim 1, wherein the lithium salt is present in the electrolyte at a concentration in the range of about 0.1 M to about 3 M.

10. The electrolyte of claim 1, wherein the non-aqueous solvent comprises one or more solvent selected from the group consisting of an ether, a carbonate ester, a nitrile, a sulfoxide, a sulfone, a fluoro-substituted linear dialkyl carbonate, a fluoro-substituted cyclic alkylene carbonate, a fluoro-substituted sulfolane, and a fluoro-substituted sulfone.

11. The electrolyte of claim 1, wherein the non-aqueous solvent comprises one or more carbonate esters selected from the group consisting of ethylene carbonate, propylene carbonate, dimethyl carbonate, diethyl carbonate, and ethylmethyl carbonate.

12. The electrolyte of claim 1, wherein the non-aqueous solvent comprises ethylene carbonate (EC) and ethyl methyl carbonate (EMC) in an EC:EMC ratio of about 3:7 (v:v).

13. The electrolyte of claim 12, wherein the lithium salt comprises about 1 to 1.5 M LiPF$_6$ and the compound of Formula (I) comprises about 0.3 to 0.5 M CP-Cl.

14. The electrolyte of claim 12, wherein the lithium salt comprises about 1 to 1.5 M LiPF$_6$ and the compound of Formula (I) comprises about 0.3 to 0.5 M CP-TFSI.

15. An electrochemical cell comprising an anode, a cathode, a lithium ion-porous membrane between the anode and the cathode, and the electrolyte of claim 1 contacting the anode, the cathode, and the membrane.

16. A battery comprising a plurality of electrochemical cells of claim 15 electrically connected together in series, in parallel, or in both series and parallel.

17. An electrolyte for a lithium-ion electrochemical cell comprising a non-aqueous solution of a lithium salt and a redox shuttle salt in an organic solvent wherein the redox shuttle salt comprises tris(diethylamino)cyclopropenium chloride (CP-Cl), which has the formula:

CP-Cl and wherein the concentration of the redox shuttle salt is about 0.3 to 0.5 M; the non-aqueous solvent comprises one or more carbonate esters selected from the group consisting of ethylene carbonate, propylene carbonate, dimethyl carbonate, diethyl carbonate, and ethylmethyl carbonate; and the lithium salt comprises about 1 to 1.5 M LiPF$_6$.

18. The electrolyte of claim 17, wherein the non-aqueous solvent comprises ethylene carbonate (EC) and ethyl methyl carbonate (EMC) in an EC:EMC ratio of about 3:7 (v:v).

19. The electrolyte of claim 9, wherein the non-aqueous solvent comprises ethylene carbonate (EC) and ethyl methyl carbonate (EMC) in an EC:EMC ratio of about 3:7 (v:v).

20. An electrolyte for a lithium-ion electrochemical cell comprising a non-aqueous solution of a lithium salt and a redox shuttle salt in an organic solvent; wherein the redox shuttle salt comprises tris(diethylamino)cyclopropenium bis(trifluoromethanesulfonyl)imidate (CP-TSFI), which has the formula:

CP-TSFI and wherein the concentration of the redox shuttle salt is about 0.3 to 0.5 M; the non-aqueous solvent comprises one or more carbonate esters selected from the group consisting of ethylene carbonate, propylene carbonate, dimethyl carbonate, diethyl carbonate, and ethylmethyl carbonate; and the lithium salt comprises about 1 to 1.5 M $LiPF_6$.

* * * * *